US00PP17578P2

(12) United States Plant Patent
Friday

(10) Patent No.: US PP17,578 P2
(45) Date of Patent: Apr. 10, 2007

(54) PEACH TREE NAMED "P.F. 19-007"

(50) Latin Name: *Prunus persica*
Varietal Denomination: P.F. 19-007

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 306 days.

(21) Appl. No.: 10/702,922

(22) Filed: Nov. 7, 2003

(51) Int. Cl.
*A01H 5/00* (2006.01)

(52) U.S. Cl. ..... Plt./197

(58) Field of Classification Search ..... Plt./197, Plt./196
See application file for complete search history.

*Primary Examiner*—Anne Marie Grunberg
*Assistant Examiner*—Georgia Helmer

(57) ABSTRACT

A new and distinct variety of peach, *Prunus persica,* tree having the following unique combination of desirable features:

1. The limbs of the tree naturally grow at wide angles creating a wide-spreading tree.
2. A fruit with a very dark skin that remains firm when ripe.
3. A highly colored, peach cultivar that matures a few days before the variety P.F. 23 U.S. Plant Pat. No. 164 and which hangs on the tree for many days staying extremely firm.

1 Drawing Sheet

Botanical classification: *Prunus persica.*

ORIGIN OF VARIETY

The new peach tree (hereinafter referred to as the 'P.F. 19-007' peach tree) was originated by Paul Friday in an experimental orchard, which is maintained for the purposes of breeding peach trees, located in Coloma, Mich. Coloma is located in the southwest section of Michigan, USDA Hardiness Zone 6a, with observed temperature ranges of minus 12 degree Fahrenheit to 90 degree Fahrenheit, also with annual rainfall of about 40 inches.

In an ongoing mass selection breeding program, unpatented superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application 'P.F. 19-007', was a selection from one such unpatented seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard of Paul Friday Farms, Inc., located in Coloma, Mich. The asexual propagation demonstrates that such reproduction of the characteristic of the tree are consistent and are established and transmitted through succeeding propagation.

SUMMARY OF THE VARIETY

The new and distinct variety of peach tree is above average height and of spreading growth and a regular and productive bearer of peaches. A distinct characteristic of the 'P.F.19-007' peach tree is its medium vigor having growth of about twenty-four inches (24') per year. The blossoms bloom in mid-season and are characterized by being contracted or partially spread to approximately ¾-inch when in full bloom. At the same time five petals of the blossoms are of lesser length than the length of petals of the normal showy blossom as exemplified by the 'Loring' (non-patented) peach blossom.

The blossoms of the present peach tree at full bloom may be characterized as being non-showy. More specifically, the blossoms of the present peach tree have radically projecting and angularly Spaced five blossom petals to form a blossom having a diameter of about ¾-inch across the blossoms.

The flesh of the fruit of the present peach tree is very firm and is yellow.

The skin is smooth having moderate to little down and is very dark red color overlying a yellow ground color. The yellow background covers approximately ten percent (10%) of its surface at maturity. At maturity, the peach is spherical having an average diameter of about 2⅞".

The fruit produced by this tree has firm, and non-melting flesh, and thereby has the attendant resistance to blemishes and soft spots in harvesting, shipping, and handling due to bruising. The firmness of the fruit flesh is sufficient to allow the flesh to yield and be restored when bumped or dropped without the resulting soft spots as would be experienced in most late season peaches of this market class. Thus, fruit of this tree remains more attractive to the ultimate buyer, the consumer, and thereby will command premium prices for the late fresh desert market.

The fruit matures a few days before the variety P.F. 23 U.S. Plant Pat. No. 164 and will hang on the tree for many days, staying extremely firm. The fruit as mentioned heretofore is of dark red color overlying a yellow background which covers only about ten percent (10%) of its surface and has a very attractive appearance.

BRIEF DESCRIPTION OF THE PHOTOGRAPHS

In the accompanying photographic illustrations, the top photograph shows the leaves of the plant, depicting both upper and lower sides, length of the leaves and internodes length.

The bottom photograph shows three whole peaches of this cultivar depicting dark red color. A fruit has been split on plane ninety degrees to the suture plane to depict the fruit flesh in cross section. The conformance of the pit cavity is illustrated as is the desirable ratio of the size of the stone to the fruit size of this tree. A ruler has been placed in the photograph showing the large size of the fruit.

DESCRIPTION OF VARIETY

The detailed botanical description of the foliage and fruit of the new variety of peach tree is Based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. 19-007'.

Tree:
- *Age.*—Ten (10) years.
- *Height.*—Unpruned 11½ feet.
- *Width.*—Unpruned 12 feet.
- *Size.*—Medium.
- *Vigor.*—Medium.
- *Density.*—Medium.
- *Form.*—Spreading.
- *Production.*—Very good, requires heavy thinning.
- *Bearer.*—Good.
- *Disease resistance to bacterial leaf and fruit spot.*—Good resistance.

Trunk:
- *Bark.*—Gray (pantone # 416).
- *Size.*—Medium.
- *Surface.*—Smooth.
- *Diameter.*—4"–18" above ground at 10 years of age.
- *Lenticels.*—Smooth.
- *Lenticels color.*—Pantone # 450.
- *Lenticels size.*—¼" to ⅜".

Branches:
- *Size.*—Medium — 2 7/16" diameter at trunk union.
- *Surface.*—Smooth.
- *Lenticels per square inch on branch.*—Eight (8).
- *Lenticels color.*—Pantone # 407.
- *Lenticels size.*—⅛" to 3/16".
- *Branch color.*—Gray (Pantone # 416).
- *Crotch angles.*—70 degree angle.
- *Internode length.*—9/16".

Leaves:
- *Size.*—Average length 5½" — average width 1½".
- *Form.*—Lanceolate.
- *Thickness.*—Medium.
- *Texture.*—Glabrous.
- *Margins.*—Serrate.
- *Petiole length.*—7/16".
- *Glands.*—1 to 2 eithe side of the petiole, noteably not very apparent on the leaf.
- *Gland shape.*—Round.
- *Gland color.*—Noteably Green.
- *Color.*—Adaxial (top) of the leaf green (Pantone # 378).
- *Color.*—Abaxial (bottom) of leaf green (Pantone # 391).

Flowerbuds:
- *Size.*—½" long — 5/16" wide.
- *Shape.*—Ovid.
- *Color.*—Pink (Pantone # 212).

Flowers:
- *Blooming period.*—Apr. 24, 2003 to Apr. 30, 2003.
- *Bloom size.*—¾" diameter.
- *Size of petals.*—½" long — ¼" wide.
- *Shape of petals.*—Cupped.
- *Number of petals.*—Five (5).
- *Sepal size.*—¼" long — 3/16" wide.
- *Sepal shape.*—Cupped.
- *Sepal color.*—Green (Pantone # 384).
- *Number of anthers.*—Forty (40).
- *Anthers color.*—Brown (Pantone # 132).
- *Number of stamens.*—Forty (40).
- *Stamen length.*—5/16".
- *Stamen color.*—Dark charcoal (Pantone #417).
- *Pistil length.*—⅜".
- *Pistil color.*—Light green (Pantone #387).
- *Pollen.*—Present.
- *Flower color.*—Pink (Pantone # 243).
- *Flowers per cluster.*—Two (2).
- *Fragrance.*—Very Fragrant.

Fruit:
- *Maturity when described.*—Full Maturity.
- *Date of first picking.*—Aug. 22, 2003.
- *Date of last picking.*—Aug. 28, 2003.
- *Size.*—Average 2¾".
- *Form.*—True spherical shape.
- *Suture.*—Not pronounced.
- *Weight.*—Average 7.3 oz.

Skin:
- *Thickness.*—Medium as compared to the species.
- *Texture.*—Firm.
- *Tendency to crack.*—None.
- *Down.*—Moderate.
- *Color.*—90% Red (Pantone # 181) over yellow (Pantone # 130).

Flesh:
- *Texture.*—Extremely firm, non-melting, free of fiber.
- *Ripens.*—Evenly.
- *Flavor.*—Very good.
- *Aroma.*—Pleasant.
- *Eating quality.*—Excellent.
- *Color.*—Dark yellow (Pantone # 131) with dark red around pit.
- *Pit cavity color.*—Dark Red (Pantone # 187).

Stone:
- *Type.*—Freestone.
- *Size.*—1 15/16" long — 1" wide — ¾" thick.
- *Form.*—Ovid.
- *Base.*—Flat.
- *Apex.*—Pointed.
- *Sides.*—About even.
- *Surface.*—Furrowed.
- *Color.*—Brow (Pantone # 180).
- *Tendency to crack.*—About 4%.

*Kernel.*—5/8" long — 1" wide — 3/4" thick (about 3 out of 10 Double Kernel).

Use: Dessert.

Shipping quality: Very Good.

Keeping quality: Very good — fruit has been kept 2 weeks and longer without losing texture or flavor.

Disease resistance: The fruit is resistant to brown rot.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

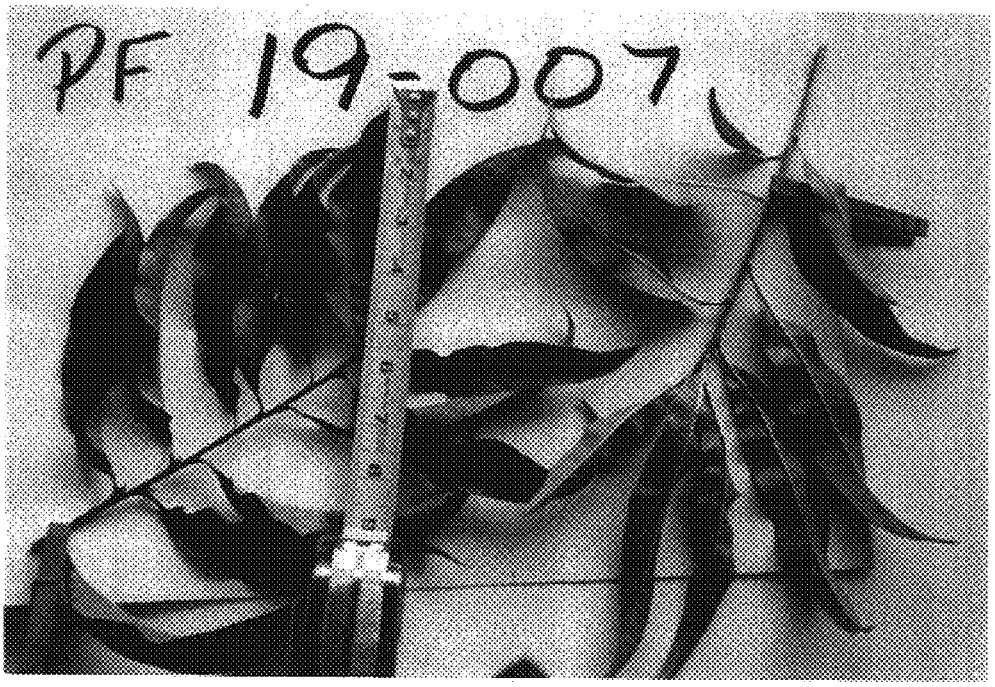
PF 19-007
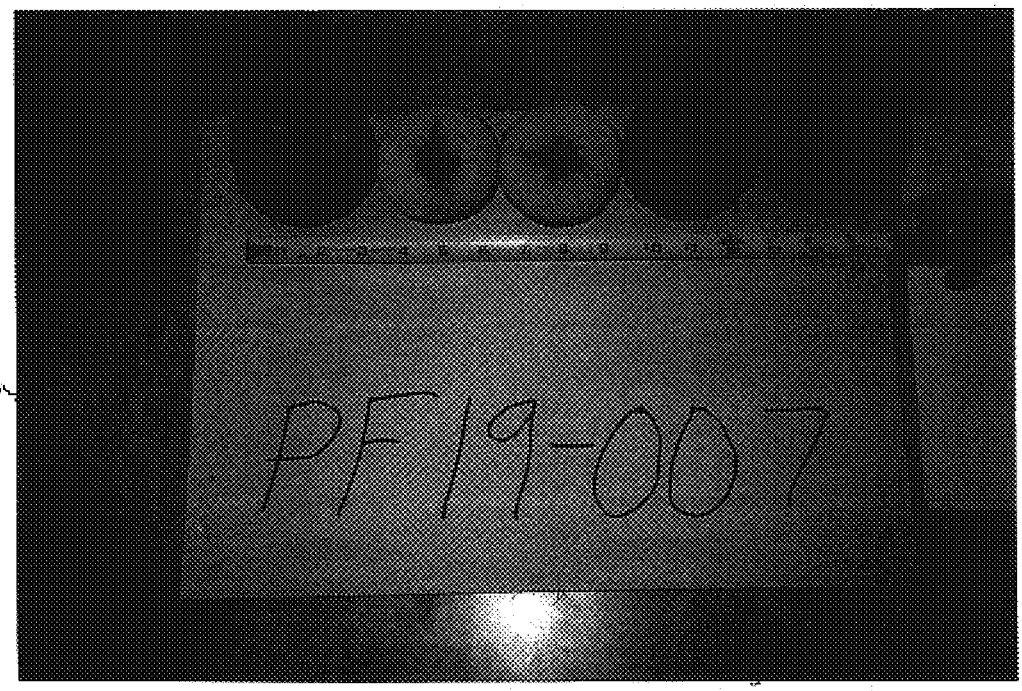
PF 19-007